United States Patent [19]

Mawhinney et al.

[11] Patent Number: 4,469,794

[45] Date of Patent: Sep. 4, 1984

[54] SILYLATION OF INORGANIC OXY-ANIONS

[75] Inventors: Thomas P. Mawhinney, Columbia, Mo.; Michael A. Madson, Clear Lake, Iowa

[73] Assignee: The Curators of the University of Missouri, Columbia, Mo.

[21] Appl. No.: 353,359

[22] Filed: Mar. 1, 1982

[51] Int. Cl.³ ............................................. G01N 31/08
[52] U.S. Cl. .................................. 436/127; 436/161; 436/174
[58] Field of Search ................ 436/89, 90, 174, 161, 436/100–102, 127, 129

[56] References Cited

PUBLICATIONS

Mawhinney, Journal of Chromatography, 257, (1983), 37–44.

Barzan et al., Journal of Chromatography, 236, (1982), 201–207.

Donike et al., Journal of Chromatography, 202, (1980), 483–486.

Kelly et al., Analytical Chemistry, vol. 48, No. 3, Mar. 1976.

Knapp, "Handbook of Analytical Derivatization Reactions", John Wiley & Sons, 1979, pp. 8–10, 387–404.

Primary Examiner—Arnold Turk
Attorney, Agent, or Firm—Grace J. Fishel

[57] ABSTRACT

An improved method for analyzing inorganic oxyanions by silylation with silylating agents of the formulae:

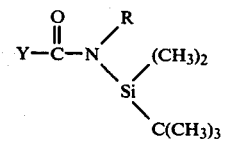

and

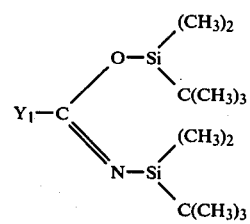

wherein R is lower alkyl, Y is hydrogen, lower alkyl or perfluoroloweralkyl and $Y_1$ is hydrogen or lower alkyl.

6 Claims, 1 Drawing Figure

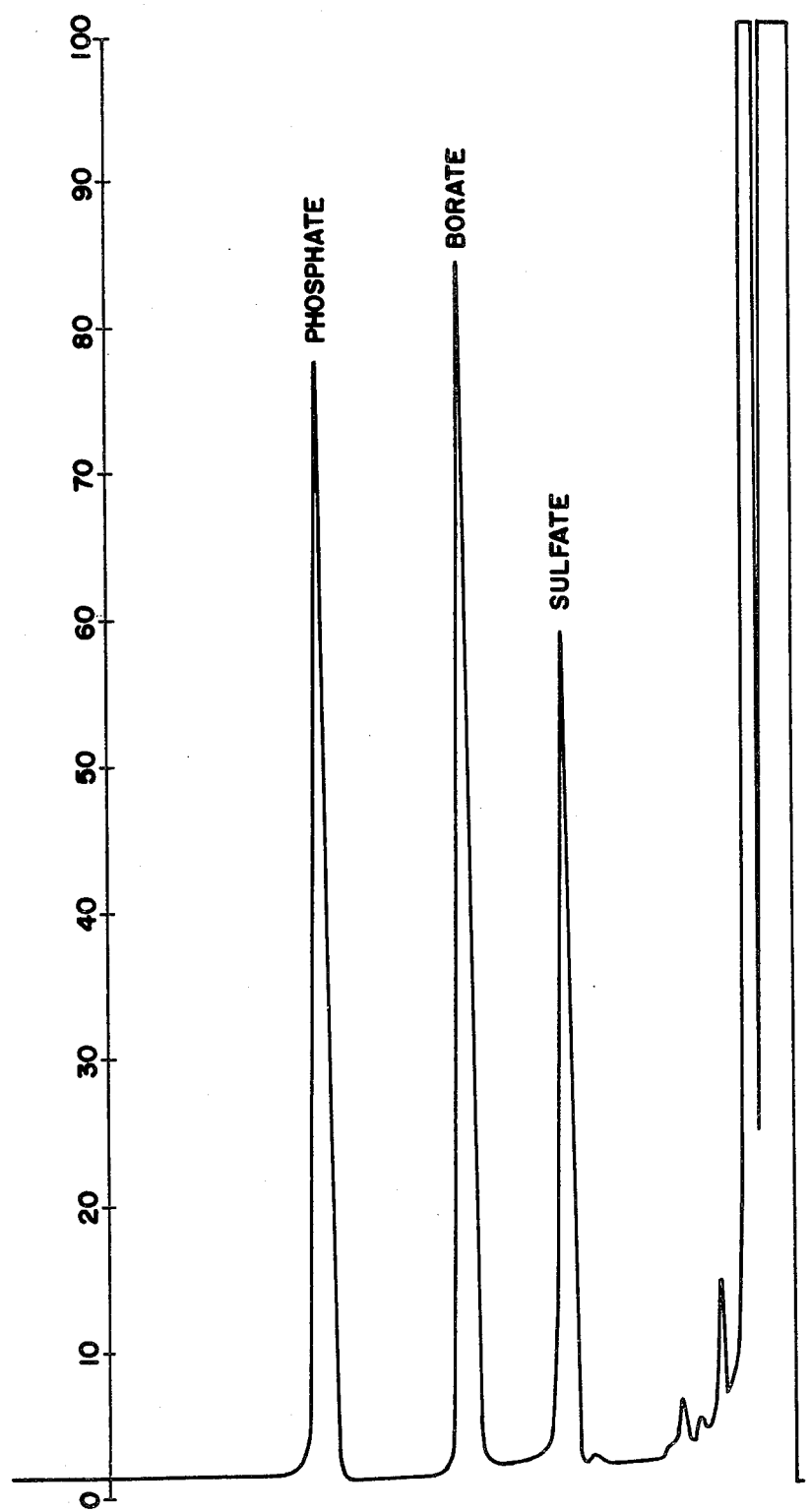

SILYLATION OF INORGANIC OXY-ANIONS

The present invention relates to the analysis of inorganic oxy-anions by silylation. It particularly relates to the silylation of inorganic oxy-anions for analysis by gas chromatography.

BACKGROUND OF THE INVENTION

The replacement of an active hydrogen by a trialkylsilyl group reduces the polarity of a compound and decreases the possibility for hydrogen bonding. Consequently, where there is marked intermolecular hydrogen bonding in the parent compound the silylated derivative is usually more volatile. The greatest use of silylation has been for gas chromatography.

Of particular utility among the many trialkyl silylating agents are those having a t-butyldimethylsilyl group. The most common of these agents is t-butyldimethylsilyl chloride which in the presence of a base such as imidazole or pyridine in a solvent such as N,N-dimethylformamide has been successfully used in the analysis of many compounds containing an active hydrogen. Silylating agents having a t-butyldimethylsilyl group are preferred over their trimethylsilyl counterparts because of the ease with which the t-butyldimethylsilyl group can be removed under relatively mild acidic or neutral conditions, and the relative high stability of the t-butyldimethylsilyl derivative to alkaline conditions, to hydrogenolysis and to solvolysis.

While trimethylsilyl reagents such as N,O-bistrimethylsilylacetamide will trimethylsilylate phosphoric acid, boric acid and others, the silylated oxy-anions are unstable and degrade to some extent on a gas chromatograph. The trimethylsilyl derivatives of sulfuric acid and sulfurous acid degrade rapidly and will destroy most gas chromatograph columns after several injections. On the other hand, silylated oxy-anions of sulfuric acid, phosphoric acid, boric acid, phosphorous acid, carbonic acid and the like are not formed at all with t-butyldimethylsilyl chloride even in the presence of a base such as imidazole in N,N-dimethylformamide.

In view of the above, it is an object of the present invention to provide an improved method for analyzing inorganic oxy-anions. Other objects and features will be in part apparent and in part pointed out hereinafter. The invention accordingly comprises the methods hereinafter described, the scope of the invention being indicated in the subjoined claims.

THE PRESENT INVENTION

The present invention provides an improved method for analyzing inorganic oxy-anions with t-butyldimethylsilyl donars which do not have the disadvantages of the presently used silylating agents. The method is rapid and accurate to the nanogram scale. FIG. 1 shows a typical run for a mixture of inorganic oxy-anions in accordance with the present invention as t-butyldimethylsilyl derivatives by gas chromatography on a 3% SP-2250 column programmed from 120° C. to 190° C. at 8 degrees/minute.

In accordance with the present invention inorganic oxy-anions are reacted with a silylating agent of the formulae:

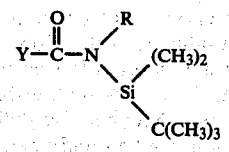

and

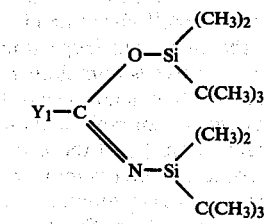

wherein R is lower alkyl having from 1 to 5 carbon atoms, Y is hydrogen, lower alkyl containing 1 to 5 carbon atoms or perfluoroloweralkyl having 1 to 5 carbon atoms, and $Y_1$ is hydrogen or lower alkyl having from 1 to 5 carbon atoms. The lower alkyl groups may be branched or straight-chained and include methyl, ethyl, propyl, isopropyl, butyl, sec-butyl, amyl, isoamyl and the like. Preferably, R is methyl and Y is hydrogen, methyl or trifluoromethyl and $Y_1$ is methyl.

Most of these compounds are clear liquids, easily transferable with a gas-tight syringe, and are readily soluble in most organic solvents.

The compounds are prepared by the reaction of t-butyldimethylsilyl chloride with an amide of the structure:

$$Y-\overset{O}{\underset{\|}{C}}-N\diagup{\overset{R}{\diagdown H}}$$

or $$Y_1-\overset{O}{\underset{\|}{C}}-N\diagup{\overset{R}{\diagdown H}}$$

in the presence of a base which will not react with t-butyldimethylsilyl chloride. Suitable bases include sodium hydride, potassium hydride, lithium hydride, and tertiary amines such as pyridine, trimethylamine, triethylamine, N-methylmorpholine and the like and the product compounds may be isolated or, in some cases, formed in situ before they are used as silylating agents.

The above-described t-butyldimethylsilyl donars are used to analyze inorganic oxy-anions by silylating the inorganic oxy-anions under silylating conditions. As such, the process can be used to analyze for sulfate, borate, phosphate, arsenate, arsenite, molybdate, oxalate, phosphite, sulfite, selenate, selenite, carbonate and so forth. Since the t-butyldimethylsilyl donars and their derivatives are more stable to moisture than their trimethylsilyl counterparts, the silylation can be conducted in the presence of a small amount of water. An excess amount of t-butyldimethylsilyl donar is added to the sample above that necessary to react with the active hydrogens in the sample so that even though the sample is slightly wet, silylation of the sample is driven to completion.

Since the t-butyldimethylsilyl donars are flammable, the silylation is carried out under a nitrogen blanket. When the t-butyldimethylsilyl donar is a liquid, e.g. when the donar is N-methyl-N-t-butyldimethylsiliyltrifluoroacetamide, N-methyl-N-t-butyldimethylsilylacetamide or N,O-bis-t-butyldimethylsilylacetamide, the silylation can be conducted in pure silylating agent without a solvent. In other cases, it is preferred that the reaction be carried out in a solvent such as acetonitrile or N,N-dimethylformamide.

Silylation of the inorganic oxy-anions occurs very quickly and in most cases is complete within 1 minute. A sample of the reaction mixture can be injected directly into a gas chromatograph without further treatment. The solvent (if any) and the excess t-butyldimethylsilyl donar come off the column first, precondition it and removing any polar functions. Because of the increased molecular weight of the derivative, there is a concomitant increase in measuring capability and in most cases it is possible to measure amounts of oxyanion down to 10 to 50 nanograms. The eluant from the chromatograph can then be analyzed in a mass spectrometer where the identification of the oxy-anions is simple because of the ease with which the t-butyl group is lost leaving ions with a mass less than 57.

The invention will become clearer from the following examples which illustrate the invention.

EXAMPLE 1

N-methyl-N-t-butyldimethylsilyltrifluoroacetamide

To 800 ml of dry benzene:acetonitrle (v/v, 1:1) was added 127 g (1.0 mole) of N-methyl-trifluoroacetamide. To this solution, while stirring and maintaining the temperature at 0 degrees C., was slowly added 23.5 g (0.98 mole) of sodium hydride. The solution was then stirred for 4 hours at 4 degrees C. At this time, 173.34 g (1.15 mole) of t-butyldimethylsilyl chloride was added in four equal aliquots over a period of 80 minutes. After the last addition the solution was stirred for 2 hours at 4 degrees C. The precipitate of sodium chloride was then removed from the reaction mixture by filtration under dry nitrogen and the resulting filter cake washed twice with 100 ml each of dry benzene. Washings and filtrate were combined and concentrated. The remaining yellow solution was fractionally distilled with the distillate at 158-172 degrees C. being collected. Redistillation of this fraction gave the desired product.

Yield, 91.3%; b. p. 168-170 degrees C. (760 mm); $d_4^{20}$ 1.121. $^1H$ NMR (CDCl$_3$) $\delta$0.28 (tetramethylsilane having $\delta$0.00), (s,6H, Si(CH$_3$)$_2$), 0.98 (s,9H,SiC(CH$_3$)$_3$), 3.08 (s,3H,N(CH$_3$); mass spectrum, m/e (relative intensity) 241 (M+, 18), 226 (22), 184 (100), 147 (79), 145 (52), 130 (18), 127 (33), 113 (20).

Analysis calculated for C$_9$H$_{18}$F$_3$NOSi: C, 44.79; H, 7.52; N, 5.80; Si, 11.64.
Found: C, 44.47; H, 7.46; N, 5.69; Si, 11.50.

EXAMPLE 2

N-methyl-N-t-butyldimethylsilylacetamide

To a vigorously stirred solution of 73.1 g (1.0 mole) N-methylacetamide dissolved in 1400 ml of dry triethylamine was added 196 g (1.30 mole) of t-butyldimethylsilyl chloride. The flask was purged with dry nitrogen and then equipped with a drying tube. Hard stirring of the mixture was continued for 24 hours at room temperature. Then, under a layer of dry air, the reaction mixture was filtered to remove the precipitate of triethylamine hydrochloride. The resulting filter cake was then washed three times with 150 ml each of dry triethylamine. The filtrate and washings were combined and reduced in volume by distillation at 35 degrees C. at 10 mm Hg. The remaining straw colored liquid was then fractionally distilled.

Yield, 88%, b. p. 57-59 degrees C. (1.0 mm); $d_4^{20}$ 0.8997. H$^1$ NMR (CDCl$_3$) $\delta$0.26 (s, 6H, N-Si(CH$_3$)$_2$), 0.94 (s,9H,N-Si(CH$_3$)$_3$), 2.05 (s,3H,CH$_3$-C), 2.79 (s,3H,N(CH$_3$)); mass spectrum, m/e (relative intensity) 187 (M+, 11), 127 (17), 130 (100), 147 (74), 73 (66), 59 (93).

Analysis calculated for C$_9$H$_{21}$NOSi: C, 57.70; H, 11.30; N, 7.48; Si, 14.99.
Found: C, 57.32; H, 11.12; N, 7.59; Si, 14.96.

EXAMPLE 3

N-methyl-N-t-butyldimethylsilylformamide

The procedure of Example 2 was followed except that 59.01 g (1.0 mole) of N-methylformamide was used in place of N-methylacetamide.

Yield, 93%, b. p. 84-85 degrees C. (1.2 mm); m. p. 32 degrees C. (moist solid). $^1H$ NMR (CDCl$_3$) 0.29 (s,6H,N-Si(CH$_3$)$_2$), 0.93 (s,9H,SiC(CH$_3$)$_3$), 2.76 (s,3H,N(CH$_3$)), 8.27 (s,1H,H-C); mass spectrum, m/e (relative intensity) 173 (M$^+$, 18), 158 (22), 147 (67), 116 (100), 59 (86).

Analysis calculated for C$_8$H$_{19}$NOSi: C, 55.44; H, 11.05; N, 8.08; Si, 16.20.
Found: C, 55.63; H, 10.88; N, 8.19; Si, 15.99.

EXAMPLE 4

N,O-bis-t-butyldimethylsilylacetamide

The procedure of Example 2 was followed except that 29.5 g (0.5 mole) of acetamide was used in place of N-methylacetamide.

Yield, 88.7%; b. p. 91 $\propto$ 92 degrees C. (2.0 mm); $d_4^{20}$ 0.859. $^1H$ NMR (CDCl$_3$) $\delta$0.06 (s,6H,O-Si(CH$_3$)$_2$), 0.22 (s,6H,N-Si(CH$_3$)$_2$), 0.87 (s,18H, (Si-C(CH$_3$)$_3$)$_2$), 1.93 (s,3H, CH$_3$-C); mass spectrum, m/e (relative intensity) 287 (M+, 15), 272 (13), 230 (100), 189 (33), 155 (78), 147 (74), 116 (22).

Analysis calculated for C$_{14}$H$_{33}$NOSi$_2$: C, 58.47; H, 11.57; N, 4.87; Si, 19.53.
Found: C, 58.28; H, 11.52; N, 11.61; Si, 19.44.

EXAMPLE 5

In accordance with the present invention, the t-butyldimethylsilyl donars prepared in the foregoing examples were used to silylate a sample containing a mixture of inorganic oxy-anions. The silylations were performed under dry nitrogen in TEFLON faced septum capped reaction vials and flasks. Prior to silylation, the sample was dissolved in a minimal amount of either dry acetonitrle or N,N-dimethylformamide. Silylation was accomplished by adding 10.0 equivalents based on the number of silylatable functions of a t-butyldimethylsilyl donar of the above formulae. While the t-butyldimethylsilylating agent may be used alone, it is preferred to add a non-interfering acid as a catalyst such as 1% by weight of t-butyldimethylsilyl chloride.

The t-butyldimethylsilyl donar reacts quickly with all common inorganic oxy-anions at room temperature producing derivatives that when chromatographed yield very symmetrical, sharp peaks for each inorganic oxy-anion as shown in FIG. 1 when the reaction mixture is chromatographed on a column. Separation of the inorganic oxy-anions is ideal with substantially no peak tailing and no degradation products. Samples of the eluant from the gas chromatograph were then analyzed in a mass spectrometer.

In view of the above, it will be seen that the several objects of the invention are achieved and other advantageous results attained. As various changes could be made in the above methods without departing from the scope of the invention, it is intended that all matter contained in the above description or shown in the accompanying drawing shall be interpreted as illustrative and not in a limiting sense.

What is claimed is:

1. In a method for analyzing inorganic oxy-anions by silylating said inorganic oxy-anions under silylating conditions with a silylating agent, the improvement which comprises selecting the silylting agent from compounds having the structure:

$$Y-\underset{\underset{O}{\|}}{C}-N\underset{Si}{\overset{R}{\diagup}}\underset{C(CH_3)_3}{\overset{(CH_3)_2}{\diagup}}$$

or

-continued $$Y_1-C\underset{N-Si}{\overset{O-Si}{\diagdown}}\underset{C(CH_3)_3}{\overset{(CH_3)_2}{\diagdown}}\underset{C(CH_3)_3}{\overset{(CH_3)_2}{\diagdown}}$$

wherein:
R is lower alkyl having 1 to 5 carbon atoms,
Y is hydrogen, lower alkyl having 1 to 5 carbon atoms, or perfluoroloweralkyl having 1 to 5 carbon atoms, and
$Y_1$ is hydrogen or lower alkyl having 1 to 5 carbon atoms.

2. The method according to claim 1 wherein R is methyl.

3. The method according to claim 2 wherein Y is hydrogen.

4. The method according to claim 2 wherein Y is methyl.

5. The method according to claim 2 wherein Y is trifluoromethyl.

6. The method according to claim 1 wherein $Y_1$ is methyl.

* * * * *